(12) United States Patent
Majeed et al.

(10) Patent No.: US 8,383,594 B2
(45) Date of Patent: *Feb. 26, 2013

(54) PEPTIDES MODIFIED WITH TRITERPENOIDS AND SMALL ORGANIC MOLECULES: SYNTHESIS AND USE IN COSMECEUTICALS

(75) Inventors: Muhammed Majeed, Piscataway, NJ (US); Renukeshwar H Chandramouli, Bangalore (IN); Kalyanam Nagabhushanam, Piscataway, NJ (US); Rattan Sood, Bangalore (IN); Subbalakshmi Prakash, Piscataway, NJ (US); Susmitha Anand, Bangalore (IN)

(73) Assignee: Sami Labs Limited, Bangalore (IN)

( * ) Notice: Subject to any disclaimer, the term of this patent is extended or adjusted under 35 U.S.C. 154(b) by 539 days.

This patent is subject to a terminal disclaimer.

(21) Appl. No.: 11/835,165

(22) Filed: Aug. 7, 2007

(65) Prior Publication Data

US 2010/0034758 A1 Feb. 11, 2010

(51) Int. Cl.
*A61K 38/08* (2006.01)
*A61K 8/64* (2006.01)

(52) U.S. Cl. ..................... 514/21.8; 514/18.6
(58) Field of Classification Search .......... None
See application file for complete search history.

(56) References Cited

U.S. PATENT DOCUMENTS 6,620,419 B1 * 9/2003 Lintner .................. 424/401
2009/0169651 A1 * 7/2009 Majeed .................. 424/727

* cited by examiner

*Primary Examiner* — Cecilia Tsang
*Assistant Examiner* — Ronald Niebauer
(74) *Attorney, Agent, or Firm* — Arent Fox LLP

(57) ABSTRACT

The present invention relates to the Synthesis of Triterpenoid peptides and mechanism of action for Anti ageing and skin care. The present invention is directed towards anti-aging skin care compositions comprising peptides which are made by linking herbal actives to a pentapeptide for enhanced anti ageing activity by regenerating the dermal matrix. In detail, the present invention relates to the synthesis of Triterpenoid peptides, providing an enhanced and synergistic activity for reducing the consequences of ageing such as appearance of fine expression lines and wrinkles on the skin by cosmetic modes of application. The Triterpenoid peptides of the present invention with its novel dual action mode can be used for skin ageing & collagen insufficiency. Its Triterpenoid group acts by preventing oxidation and excess activity of serine proteases like elastase and collagenase that result in wrinkling of skin. With added peptides which boost the collagen and other matrix protein, Triterpenoid peptides provide a complete protection against pre mature ageing and functions as a best anti ageing ingredient.

4 Claims, 1 Drawing Sheet

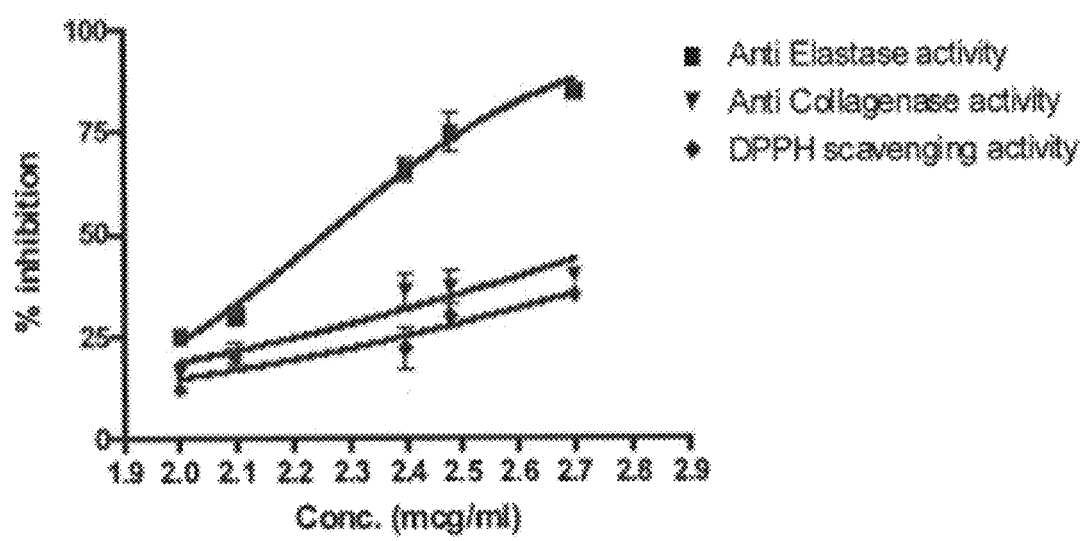

SEQUENCE LISTING

<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Thr Thr Lys Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Thr Thr Lys Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Thr Thr Lys Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Thr Thr Lys Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Thr Thr Lys Ser
1               5

<210> SEQ ID NO 6
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Lys Thr Thr Lys Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Thr Thr Lys Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Thr Thr Lys Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Thr Thr Lys Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Thr Thr Lys Ser
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Thr Thr Lys Ser
1               5
```

```
<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Thr Thr Lys Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Thr Thr Lys Ser
1               5
```

PEPTIDES MODIFIED WITH TRITERPENOIDS AND SMALL ORGANIC MOLECULES: SYNTHESIS AND USE IN COSMECEUTICALS

FIELD OF INVENTION

This invention relates to the Synthesis and application of peptides for anti-aging skin care and to their use in improving the condition and appearance of skin. This present invention comprises of Synthesis of peptides linked to Herbal actives for Anti ageing and skin care together with the mechanism of action. The peptides containing the Actives of Herbal extracts of the present invention can be effectively used in reducing the signs of ageing due to oxidation, collagen insufficiency and excess activity of serine proteases like elastase and collagenase that results in wrinkling of skin, fine expression lines and pre mature ageing.

The complementary activities of the herbal actives and the peptide to which they are linked respectively enhance the Anti ageing activity of the resulting peptides by employing various modes of action.

BACKGROUND OF THE INVENTION

The appearance and condition of the skin may be degraded through the effects of environmental factors, either naturally occurring (sunlight, wind abrasion, humidity, etc.) or man-made (heating, air condition, pollutants, etc.), pathological processes such as dermatological diseases, or the normal aging process. The various insults to which the skin is exposed may act individually or synergistically. To ameliorate or prevent the deterioration of skin quality that may occur over time, consumers have increasingly sought new and/or improved cosmetic compositions and cosmetic methods for skin care. Such products or methods are designed to prevent, delay or reverse the visible signs of the aging process, such as the appearance of wrinkles, lines, loss of skin tone, thinning of the skin, hyper pigmentation or mottling, and age spots. Such products or methods are further designed to improve the appearance and condition of sensitive, dry or flaky skin, and/or to soothe skin that has been irritated by exposure to chemicals, wind, or sunlight, among other potential irritants.

With an aging population, there has been an increase in the study of aging as it relates to the human body and, more particularly, human skin. For example, the treatment of aging skin exhibited by the presence of fine lines, wrinkles, and the like has received a great deal of attention. The dermal signs of aging such as fine lines, wrinkles, laxity, and hyper pigmentation have been fought through many tactics including surgery, laser treatment and cosmetics. Cosmetic treatments include the use of various creams and lotions to alter the effects of dermal aging. Much of the literature in the prior art focuses on the use of a single primary component to prevent one of several deleterious aging affects. For example, one tactic has been to use one or more hydroxy acids or retinoic acid to stimulate the re-growth of dermal cells, without other components. This approach is flawed because it does not recognize that aging is caused by the deleterious interaction of multiple agents on the skin, from multiple sources, causing damage to the skin through multiple simultaneous damage pathways.

Consumers are increasingly seeking "anti-aging" products that treat wrinkling, creasing and furrowing of the skin. The advent of costly and painful cosmetic injections for treating expression lines of the face has heightened interest in finding topical alternatives that are effective and non-invasive.

Expression lines are a distinct type of wrinkle that occurs on the facial skin at an early adult age. They are related anatomically to the facial expression muscles in the periorbital, glabella, forehead, and perioral areas. The activity of these muscles during the actions of smiling, squinting, pursing of the lips, and frowning places greater physical stress upon the overlying skin than in other areas in the face. For this reason, expression lines are less responsive to those topical treatments that focus upon the non-contractile elements of cutaneous anatomy, such as the epidermis. In order to be most effective treatment of expression lines should also entail the inhibition of the facial expression muscles and the muscle fiber elements associated with the dermis. A myriad of substances that relax striated muscle fibers are described in the cosmetic prior art. The problem is that the muscle relaxants of the prior art are either slow acting, they are not potent enough, or the inhibitory effects are not cumulative. Furthermore, none of these muscle relaxants reduce facial muscle actions. A newly discovered plant extract that rapidly inhibits deformation of the dermis enables substances that repair and rejuvenate it to become more effective. An expression line is formed when a muscle of facial expression contracts or shortens itself beneath the skin and then relaxes and returns to its resting length. The skin can also shorten and rebound, but not as well as the muscle. Therefore, the skin tends to buckle and fold inward as the muscle contracts. The ability of the skin to withstand the shortening and rebounding of the underlying muscle is related to the quality and health of the upper dermis. With increasing age the thickness, elasticity, collagen content and reparative ability of the dermis diminishes. The skin can no longer rebound from this action and the fibrous intercellular matrix of the dermis weakens and breaks. At this point the skin has developed a permanent wrinkle. The wrinkle will continue to deepen as this area of the skin is subjected to the perpetual stress of facial expressions.

Anatomy of Expression Lines

The skin associated with expression lines is different histologically from that found elsewhere in the face. The interlobular septa of the sub-dermal connective tissue contains striated muscle tissue fibers (panniculus carnosus). These fibers arise from the underlying facial muscle groups. They are integrated within the collagenous network of the lower (reticular) dermis. A sub-population of dermal fibroblasts in the upper (papillary) dermis, known as "myo-fibroblasts", have inherent contractile characteristics similar to striated muscle tissue. Contractions within these dermal fibroblasts are mediated by the same neurotransmitter, i.e. acetylcholine, as the fiber elements of striated muscle. Muscle fibers within the facial skin have a direct influence on its surface smoothness, and modulating the neural motor influx to these muscle fibers causes a reduction of wrinkles. For example, patients who suffer from Bell's palsy of the facial nerve have smoother skin on the paralyzed side of the face than on the non-paralyzed side. Also, Botox™ Cosmetic injections not only immobilize the forehead and upper eyebrow muscles, but they also smooth the skin external to these muscles. Botox™ interferes with the uptake of acetylcholine within the synaptic junction of the afferent motor neuron of muscle fibers, thereby preventing contraction of muscle tissue associated with wrinkles and furrows. Boxtox™ treatment is in high demand, and thus it is the goal of cosmetic scientists to develop a topical equivalency (see A. Blitzer et al., Arch. Otolaryngol. Head Neck Surg., 119, pages 1018 to 1022 (1993) (see J. D. Carruthers et al., J. Dermatol. Surg. Oncol., 18, pages 17 to 21 (1992).

To meet consumer demand, many cosmetic compositions and cosmetic methods have been developed for skin care and treatment. However, many, if not most, of the products or treatment methods described to date lead to inadequate results or are marred by undesirable side effects. These may include irritation of the skin or adjacent mucous membranes, the production of excessive oiliness or greasiness of the skin, or discoloration of the skin.

Dermal Repair

The regenerative ability of the dermis has a critical bearing on its ability to withstand the chronic muscle contraction and relaxation of the expressive muscles. As a consequence of aging or sun damaged skin there is a reduction in the fibroblastic cells and blood vessels that are needed to rejuvenate the lower dermis. Fibroblasts in the "basal layer" of the upper dermis replicate into new cells more slowly, they loose their capacity to manufacture collagen, and they are less able to organize and preserve the collagen fiber network. Since the dermal matrix is the source of collagen and major water holding molecules, i.e. the glycosaminoglycans and hyaluronic acid, preserving it is essential to the health of the epidermis as well. Without continual replenishment of precursor proteins, disorganization and dissolution of the collagen fiber network and the extra-cellular matrix takes place. The result of this process is a flattening of the dermal-epidermal junction and a weakening of the mechanical resistance of the upper dermis. Thus, the aging skin has a much greater susceptibility for temporary deformations that occur during facial expression to become permanent (see Oikarinen, "The Aging of Skin: Chronoaging Versus Photoaging," Photodermatol. Photoimmunol. Formation, Photomed., vol. 7, pp. 3-4, 1990 and Thalmann et al. "A Computational Skin Model: Fold and Wrinkle Formation", pp. 1-5).

There are several teachings in the art (U.S. Pat. No. 6,794,362; U.S. Pat. No. 6,777,389) that discuss singular molecules or compositions thereof for enhancing the elasticity of skin or strengthening the dermis. They are formulated from peptides or peptide-like compounds that mimic the molecular composition of elastin or add to it. Mitts, et al. (U.S. Pat. No. 6,809,075) postulated that a peptide/retinoid composition could integrate within the elastin component of the dermis, thereby increasing the ability of the skin to rebound from deformation. More often the prior art teaches that natural or synthetic peptide formulations can enhance the collagen fiber network or extra-cellular substrate of the dermal matrix. Lowe, N. et al., (Pharmacology of Retinols In Skin", Vol. 3 (1989), pp. 240-248) emphasize the role of retinoids in maintaining the structural integrity of skin. However, the instability and irritation caused by retinoids are problematic. Dioguardi (U.S. Pat. No. 5,198,465) teaches a composition to increase the collagen content in the skin in general by the topical application of synthesized precursor collagen molecules and coenzymes of the collagen metabolic pathway. The premise is that direct replacement via diffusion and adsorption of precursor molecules fortifies deficient skin. A similar notion taught by Kludas (U.S. Pat. No. 5,055,298) is that a substantially natural composition can have a reparative and remodeling effect at the dermal-epidermal junction. Also, recent art (U.S. Pat. No. 6,906,036; U.S. Pat. No. 6,884,425) has taught that inhibitors of matrix metalloprotineases are capable of preventing the disruption of the dermis, healing it and facilitating a return to normal healthy skin. None of the aforementioned patents teach the capacity to stimulate fibroblastic activity and synthesis of collagen precursors; nor do they profess to restore dermal thickness and collagen fiber network.

In a recent patent, Varani, et al. (U.S. Pat. No. 6,919,072) identifies a composition of a retinoid and a matrix metalloproteinase inhibitor that inhibits collagen breakdown, promotes collagen at the content by increasing procollagen synthesis, increases keratinocytes and fibroblastic proliferation. The invention restores the thickness of the epidermal-dermal interface in chronologically aged skin and it restores collagen content within the upper dermis to normal levels. Therein lies its property to give the skin strength to withstand environmental and physical stress. As with other retinoids, the retinoid of Lowe requires prolonged application and the dermal repair is much slower than with the preferred embodiment of this application.

The significance of Peptides

The focus of the early art has been on disclosing substances that were thought to physically replenish the molecules that build new collagen or that add substances which irritate or disrupt the basal layer to effect its regeneration and healthy reconstitution. More recent art teaches the benefits of topical peptide treatments in stimulating the upper dermis to renew itself by cellular re-growth. This is supported by the knowledge that the body has naturally occurring peptides that are instrumental in stimulating the healing process following a wound to the skin. Robinson teaches (U.S. Pat. No. 6,492,326) various formulations containing combinations of palmitoyl pentapeptide-3, derivatives of pentapeptides, and mixtures thereof. Lintner (U.S. Pat. No. 6,620,419) discloses peptide formulas of the general sequence palmitoyl-lysyl-threonyl-threonyl-lysyl-serine (palmitoyl group linked to SED ID No. 13) that increase the synthesis of collagen and gylcosaminoglycans. They act synergistically to heal wrinkles and other forms of skin aging far more effectively than earlier formulations. The key difference in the Lintner teaching to that of Robinson is the addition of a fatty acid chain onto the terminal end of a pentapeptide that makes this lipophilic modified peptide very efficient at penetrating the epidermis and thus more effective in reaching the formative layers of the dermis. The net result is to increase the thickness of the skin by restoring the reparative capacity of the upper dermis. Consequently, the skin is better able to withstand the deformation imposed on it by the active contraction and relaxation of expression muscles, and micro-contractions within the skin itself.

The present invention comprises of natural fruit and plant extracts of Olive leaf, Rosemary, Sage mellisa, Tulasi, and Boswellia serrata, linked to the pentapeptide lysyl-threonyl-threonly-lysyl-serine (SEQ ID No. 13) which when applied topically to the skin, can prevent or reverse cosmetically undesirable skin conditions such as wrinkles, lines and sagging.

More comprehensive studies have found that environmental factors, such as stress, sun exposure, and impurities in food, water, and air, also adversely affect components of the epidermal and dermal layers of the skin which, in turn, impact and alter the appearance of the skin and lead to an appearance of premature aging. For example, factors such as free radicals, reactive nitrogen species ("RNS"), reactive oxygen species ("ROS"), and other oxidizing species ("OOS") that may or may not possess characteristics of each free radicals, RNS, and ROS, can adversely impact the human body including the skin. Particular factors within the groups noted above that have been found to impact and adversely affect the appearance of the skin include nitric oxide, superoxide radicals, hydrogen peroxide, and hydroxide free radicals. These factors have been variously implicated in a number of skin conditions including photodamage, general aging of the skin, contact dermatitis, wrinkling, lipid peroxidation, enzyme degradation, reduction and breakdown of collagen and/or elastin, degradation and inhibited reproduction of DNA, inflammation, and general damage to the skin tissue.

Antioxidant activity is an activity that reduces production of reactive oxygen species in the body and at the same time, prevents oxidation that causes irrecoverable damages to cells. Ground-state or triplet oxygen can be activated as a result of exposure to environmental or biochemical factors such as enzymes, reduction metabolism, chemical compounds, pollutants and photochemical reactions, and transformed into reactive oxygen species (ROS) which have a high reactivity such as superoxide radicals, hydroxy radicals, and hydrogen peroxide, accordingly it results in irreversibly disrupting cell constituents. The actions of such reactive oxygen species can be reduced by antioxidant enzymes such as superoxide dismutase (SOD), catalase and peroxidase, and antioxidant substances such as vitamin C, vitamin E and glutathione, which all form the body's defense system. However, where disorder of such a defense mechanism in the body or exposure to excessive reactive oxygen species occurs, reactive oxygen species may irreversibly disrupt lipid, protein and DNA. As a result, various diseases inclusive of aging, cancer, multiple arteriosclerosis, arthritis and Parkinson's disease are caused.

Synthetic antioxidants such as BHA (butylated hydroxy anisole), BHT (butylated hydroxy toluene) and NDGA (nordihydro-guaiaretic acid) have been developed to date. By way of examples of natural antioxidants, there are antioxidant enzymes such as superoxide dismutase, peroxidase, catalase and glutathione peroxidase, and non-enzymatic antioxidant substances such as tocopherol (vitamin E), ascorbic acid (vitamin C), carotenoid and glutathione.

However, synthetic antioxidants may cause allergic reactions and oncogenesis due to their strong toxicity in the body, and be easily disrupted by heat due to temperature sensitivity. On the other hand, natural antioxidants are safer than synthetic antioxidants in the body but have the problem of weak effect. Therefore, the development of a new natural antioxidant having no problem with safety in use and also having excellent antioxidant activity has been required. Topically-applied antioxidants do have merit for all skin types to keep skin healthy and help prevent sun damage and improve cell function.

Antioxidants have been conclusively shown to exert a positive effect on reducing skin irritation and inflammation, and that is a crucial step in creating or maintaining healthy, vibrant skin and, therefore potentially reducing wrinkles (*International Journal of Experimental Pathology*, August 2000, pages 257-263 and *Skin Pharmacology and Applied Skin Physiology*, May-August 2000, pages 143-149).

Several hundred molecules having a polyphenol (polyhydroxyphenol) structure (i.e. several hydroxyl groups on aromatic rings) have been identified in edible plants. These molecules are secondary metabolites of plants and are generally involved in defense against ultraviolet radiation or aggression by pathogens. Polyphenols are widespread constituents of fruits, vegetables, cereals, dry legumes, chocolate, and beverages, such as tea, coffee, or wine.

These compounds may be classified into different groups as a function of the number of phenol rings that they contain and of the structural elements that bind these rings to one another. Classes of polyphenols include the phenolic acids, flavonoids, stilbenes, and lignans. There are two classes of phenolic acids: derivatives of benzoic acid and derivatives of cinnamic acid.

It is indeed not practical to measure each and every one of the antioxidants in vivo. It is also now widely hypothesized that the major factor influencing oxidative stress is the overall antioxidant status of the system, which prevents diseases by eliminating free radicals and ROS. Therefore, it is essential to have a method capable of measuring collectively the extracellular antioxidant status. There are methods for measuring antioxidant status which are based on the inhibition of generated free radicals reaching the target indicator molecules, by antioxidants. The common feature for inhibition assays is to generate a free radical to react with a target molecule, thereby generating an endpoint that can be observed and quantified. Addition of antioxidants inhibits the development of this endpoint. A good example of this is the DPPH (1,1-diphenyl-2-hydrazyl) free radical scavenging activity.

Elastin, found in highest concentrations in the elastic fibers of connective tissues, is responsible for the texture and tone of the skin. ELASTASE, a serine protease enzyme, has a role in dissociating tissues which contain extensive intercellular fiber networks.

Excess elastase production will result in wrinkling of skin/premature ageing. The vital protein, collagen, maintains the skin tone and structure. COLLAGENASE is a serine protease enzyme that cleans the wound of any dead tissue leaving the wound bed ready for healing. Collagenase, intensely produced during inflammation, is known to have role in Skin wrinkling by digesting the vital protein collagen that maintains the skin tone and structure.

Another mechanism for Anti ageing is collagen enhancement in the skin. Actives that can physically replenish the molecules that build new collagen or that adds substances which irritate or disrupt the basal layer to effect its regeneration and healthy reconstitution are excellent for Anti ageing compositions. More recent art teaches the benefits of topical peptide treatments in stimulating the upper dermis to renew itself by cellular re-growth. This is supported by the knowledge that the body has naturally occurring peptides that are instrumental in stimulating the healing process following a wound to the skin. Robinson teaches (U.S. Pat. No. 6,492,326) various formulations containing palmitoyl pentapeptide-3, derivatives of pentapeptides, and mixtures thereof. Lintner (U.S. Pat. No. 6,620,419) discloses peptide formulas of the general sequence palmitoyl-lysyl-threonyl-threonly-lysyl-serine (palmitoyl group linked to SEQ ID No. 13) that increase the synthesis of collagen and gylcosaminoglycans. They act synergistically to heal wrinkles and other forms of skin aging far more effectively than earlier formulations.

SUMMARY OF THE INVENTION

The present invention is a synthesis of Pentapeptide linked to Triterpenoid actives of plant extracts like Oleanolic acid, Boswellic acid, Ursolic acid etc. The Triterpenoid actives are linked with the pentapeptide, Lysyl-Threonyl-Threonyl-Lysyl-Serine (SEQ ID No. 13) by Solution phase synthetic methodology employing Boc-chemistry.

The present invention is a topical cosmetic composition containing a safe and effective amount of plant extracts of Olive, Boswellia serrata, Sage Melissa, Rosemary and Tulsi respectively linked to an active peptide selected from groups of dermal rejuvenating peptides as described herein. The plant extracts form the critical component of the present invention that possesses antioxidant, anti inflammatory and Matrix metallo protease inhibitory properties. The preferred peptide mentioned herein is the constituent that rejuvenates the dermal matrix by enhancing collagen synthesis. The resulting Herbal active based peptide reduces the physical stress upon the upper dermis and accelerates the dermal healing of the expression lines. The peptide is combined with an inert cosmetic base suitable for topical application to the skin. Other active skin care ingredients in safe and effective amount may be added to this composition that have supportive actions and impact upon the upper dermis, dermal matrix, as well as the epidermis, but themselves do not initiate the critical effects upon the dermis or muscle tissue as taught in this invention. They are provided to: effect an increase penetration of ingredients into the skin, as a skin circulation promoter, as vitamins, as moisturizers and as skin softeners. The additional skin care actives as described herein were selected according to the criteria that they be compatible with and enhance the efficacy of the final composition to improve the smoothness appearance.

The additional skin care actives useful herein can be categorized by the benefit they contribute and/or by their mode of action. For example, Tetrahydropiperine can be used as an additional skin care active which is effective in increasing the penetration of ingredients into the skin. However, the actives can in some instances provide more than one benefit or operate via more than one mode of action. Thus, the classifications herein are made for the sake of convention and are not intended to solely limit the active agent to that particular application or applications listed. (Reference for herbal constituents from Duke, J A, CRC Handbook of Medicinal Herbs, CRC Press, Boca Raton, Fla., 1985, 110-1); also referenced (The 5th edition (1995) of the "International Cosmetic Ingredient Dictionary", edited by the American industrial association CTFA) lists about 300 plants which are added as active ingredients to cosmetic agents in various formulations. As used herein the term "improves smoothness appearance" means that the visible appearance of the skin surface during both the contraction phase of facial expressive muscles and the relaxation phase is improved as determined by visual inspection with the naked eye.

In the course of their studies on natural extracts with anti ageing properties, the present inventors propose that the peptides containing these natural extracts had complementary and enhanced anti ageing properties.

Therefore, it the object of the present invention to provide mechanisms for age defying by the compositions containing the natural extracts with anti ageing properties.

In accordance with cosmetic application aspect of the present invention, the above objects can be accomplished by inclusion of natural extracts with DPPH free radical scavenging activity, anti inflammatory properties, collagen boosting properties and serine proteases like Elastase and Collagenase inhibitory activity.

The present invention further provides a method of providing skin care benefits like reducing wrinkling and appearance of fine expression lines on the skin; delaying or preventing sagging of the skin; preventing photo damage; imparting a youthful appearance to skin; enhancing collagen deposition in skin; thereby improving skin texture, smoothness or firmness.

The inventive compositions, methods and uses described herein result in the reduction or delay in the formation of wrinkles and reduction or delay in loss of skin tone. The compositions, methods and uses described herein also improve skin texture, smoothness or firmness, and create smooth and supple skin with improved elasticity. A general improvement in the appearance, texture and condition, in particular with respect to the radiance, clarity, and general youthful appearance of skin is achieved. The present invention therefore provides a wide range of results that are collectively described as anti-aging benefits.

DEFINITIONS

The term "topical application", as used herein, means to apply or spread the compositions of the present invention onto the surface of the skin.

The term "dermatologically-acceptable," as used herein, means that the compositions or components thereof so described are suitable for use in contact with human skin without undue toxicity, incompatibility, instability, allergic response, etc.

The term "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e. to provide a reasonable benefit to risk ratio, within the scope of sound judgment of the skilled artisan.

The term "skin compatibility," as used herein means the ability of skin to tolerate long term application of topical compositions with minimal adverse skin reactions such as stinging, burning, redness, itching and folliculitis.

The term "co-administered" refers to administering the composition with a second medicinal, typically having a differing mechanism of action, using a dosing regimen that promotes the desired result. This can refer-to simultaneous dosing, dosing at different times during a single day, or even dosing on different days. The compositions can be administered separately or can be combined into a single formulation.

BRIEF DESCRIPTION OF THE DRAWINGS

FIG. 1 shows the efficacy of herbal active based peptides in anti-aging mechanisms; anti-elastase activity, anti-collagenase activity, DPPH scavenging activity.

DETAILED DESCRIPTION OF THE INVENTION

The present invention provides an anti-aging skin care Triterpenoid peptides comprising plant extracts of Olive, Boswellia serrata, Rosemary, Sage and Tulsi.

In preferred embodiments, the anti-aging skin care Triterpenoid peptides contain 1. Pentapeptide, Lysyl-Threonyl-Threonyl-Lysyl-Serine (SEQ ID No. 1) linked to the Triterpenoid Oleanolic acid (From Olive leaf extract)

2. Pentapeptide, Lysyl-Threonyl-Threonyl-Lysyl-Serine (SEQ ID No. 5) linked to the Triterpenoid Boswellic acid (3-Acetyl 11-Keto Beta Boswellic acid) (From *Boswellia serrata* extract)

3. Pentapeptide, Lysyl-Threonyl-Threonyl-Lysyl-Serine (SEQ ID No. 3) linked to the Triterpenoid, Ursolic acid (From Rosemary, Sage Melissa, Tulsi extract)

4. Pentapeptide, Lysyl-Threonyl-Threonyl-Lysyl-Serine (SEQ ID No. 9) linked to the Triterpenoid, Betulinic acid, derived naturally or by synthesis 5. Pentapeptide, Lysyl-Threonyl-Threonyl-Lysyl-Serine (SEQ ID No. 11) linked to the Lipoic acid, both racemic and (R+)-isomer 6. Pentapeptide, Lysyl-Threonyl-Threonyl-Lysyl-Serine (SEQ ID No. 12) linked to the reduced curcumin derivatives such as tetrahydrocurcumin.

The natural ingredients hereinafter referred to as "active ingredients". As indicated above, the anti-aging skin care composition of the present invention also comprises a dermatological dermatologically-acceptable vehicle. This substance may act as a diluent, dispersant or carrier for the active ingredients. The vehicle may comprise materials commonly employed in skin care products, including but not limited to water, a buffered aqueous solution, liquid or solid emollients, silicone oils, emulsifiers, solvents, humectants, thickeners, powders, propellants and the like. The vehicle may constitute from approximately 1% to 20% by volume of the anti-aging skin care composition, but preferably will constitute from approximately 5% to 50% by volume of the anti-aging skin care composition. In the absence of the other potential cosmetic or manufacturing adjuncts described below, the dermatological-acceptable vehicle will constitute the balance of the composition.

The powdered components of the anti-aging skin care composition may be dissolved in more or less vehicle to increase or decrease the strength and hence the potency of the product. Such variations in strength and potency may be highly desirable in maintaining the efficacy of the anti-aging skin care composition when treating a highly heterogeneous population comprised of individuals with large variations in skin type and condition. In preferred embodiments, the ratio of active ingredients to vehicle ranges from $1:10^6$ (weight to weight; w/w) to 1:1 (w/w).

In addition to the active ingredients described above, the anti-aging skin care composition of the present invention may optionally contain various cosmetic or manufacturing adjuncts. For example, sunscreens, skin-lightening or skin-tanning agents may also be included. The vehicle may also further include adjuncts such as antioxidants, perfumes, pacifiers, preservatives, colorants and buffers, as necessary or desirable to enhance the efficacy, storage, utility, or marketability of the anti-aging skin care composition. In preferred embodiments, the addition of perfumes or other masking agents to the skin care composition is desirable and/or necessary to reduce or block the odors associated with the presence of the active ingredients.

To prepare the anti-aging skin care composition of the present invention, a variety of techniques may be employed. For example, the active ingredients may be generally incorporated into the dermatologically-acceptable vehicle in the manner that is usual for the preparation of skin care products. Thus, the active ingredients may first be dissolved or dispersed in a portion of the water or another solvent or liquid to be incorporated into the dermatologically-acceptable vehicle. The preferred compositions for use in this manufacturing approach are oil-in-water, water-in-oil, or water-in-oil-in-water emulsions.

However, in a preferred embodiment, the active ingredients, with or without the above-described adjuncts, are maintained in a separate state from the dermatological-acceptable carrier, for example as a dry powder. The resulting anti-aging skin care composition then may be applied to the skin of the face, hands, arms, legs, neck or other areas where desirable by manual application to ensure complete and even coverage of the treated areas.

The anti-aging skin care composition of the present invention may be in the form of conventional "leave-on" skin-care products, including but not limited to aqueous solutions, creams, gels, lotions, sprays, ointments, pastes, mousses, cosmetics, etc. The anti-aging skin care composition can also be in the form of "wash-off" products, including but not limited to, a bath or shower gel, possibly containing a delivery system for the active ingredients to promote their adsorption or adherence to the skin during rinsing. Most preferably the product is a "leave-on" product; a product to be applied to the skin without a deliberate rinsing step soon after its application to the skin.

The anti-aging skin care composition of the present invention may be packaged in any suitable manner, including but not limited to, a jar, a bottle, a tube, a stick, a roller-ball applicator, an aerosol spray device, etc., in the conventional manner.

The present invention further provides a method of providing skin care benefit like, delaying or preventing wrinkling; delaying or preventing sagging; delaying or preventing photo damaged skin; imparting a youthful appearance to skin; enhancing collagen deposition in skin; enhancing tissue repair and cell growth and improving skin texture, smoothness or firmness.

In preferred embodiments, the method of the present invention may be carried out one or more times daily to the skin which requires treatment. In this method, a small volume of the anti-aging skin care composition, for example from 0.1 to 5 ml, is applied to the skin from a suitable container or applicator and spread over and/or rubbed into the skin using the hands or fingers or a suitable device. A rinsing step may optionally follow depending on whether the composition is formulated as a "leave-on" or a "rinse-off" product. The improvement in skin appearance will become apparent within one or more days of use, depending on skin condition and the concentration, amount and frequency with which the anti-aging skin care composition is used.

The inventive compositions, methods and uses described herein result in the prevention, reduction or delay in the formation of wrinkles and prevention, reduction or delay in loss of skin tone. The compositions, methods and uses described herein also improve skin texture, smoothness or firmness, and create smooth and supple skin with improved elasticity. A general improvement in the appearance, texture and condition, in particular with respect to the radiance, clarity, and general youthful appearance of skin is achieved. The present invention therefore provides a wide range of results that are collectively described as anti-aging benefits.

The inventive compositions, methods and uses described herein are further useful for topical application and for regulating skin condition, including visible and/or tactile discontinuities in skin (especially the skin surface; such discontinuities are generally undesirable). Such discontinuities may be induced or caused by internal and/or external factors, and include the signs of skin aging described herein.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g. chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g. associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, redness or discoloration (including under eye circles), blotching, sallowness, hyper pigmented skin regions such as age spots and freckles, keratoses, abnormal differentiation, hyperkeratinization, elastosis, collagen breakdown, and other histological changes in the stratum corneum, dermis, epidermis, the skin vascular system (e.g. telangiectasia or spider vessels), and underlying tissues, especially those proximate to the skin.

It is to be understood that the present invention is not to be limited to prevention, reduction or delay of the above mentioned "signs of skin aging" which arise due to mechanisms associated with skin aging, but is intended to include prevention, reduction or delay of, said signs irrespective of the mechanism of origin.

EXAMPLES

The above features and other advantages of the present invention will be more clearly understood from the following detailed description taken in conjunction with the examples. The Herbal actives and the pentapeptide used have significant anti ageing properties and the details of the same are mentioned below.

Ursolic acid: It is an off white to cream colored powder with Active component Ursolic Acid, not less than 80% pure. Source is *Rosmarinus officinalis* leaves.

Oleanolic acid: It is a cream colored powder with Active component Oleanolic acid, more than 90% pure. Source is *Olea europaea* (olive) leaves.

Boswellic acid (3-acetyl 11-Keto Beta Boswellic acid): It is the Boswellia serrata extract having Antioxidant, Anti ageing and Anti inflammatory properties. A phyto-complex combining boswellic acid and manganese (developed by L'Oreal Corporation, France) is said to reduce the appearance of expression lines and wrinkles within three weeks of use by reducing micro-contractions of muscle fibers in skin.

Pentapeptide, Lysyl-Threonyl-Threonyl-Lysyl-Serine (SEQ ID No. 13): It is a peptide of the general sequence Lysyl-Threonyl-Threonyl-Lysyl-Serine (SEQ ID No. 13) that is a product of collagen degradation (K. Katayama, J. A. Borunda, R. Raghow, A. H. Kang, J. M. Sayer, *J. Biol. Chem.*, 268, 9941 (1993).

So that it may be more readily understood, the present invention is illustrated in the following examples.

Example 1

Pentapeptide, Lysyl-Threonyl-Threonyl-Lysyl-Serine (SEQ ID No. 1) linked to the Triterpenoid Oleanolic acid (Olive leaf extract), will have the complementary properties of both the active and the peptide and as a net result will reduce or delay the symptoms of ageing by maintaining a healthy balance in the collagen synthesis and collagen breakdown in the dermal matrix of skin.

Example 2

Pentapeptide, Lysyl-Threonyl-Threonyl-Lysyl-Serine (SEQ ID No. 3) linked to the Triterpenoid, Ursolic acid (From Rosemary, Sage and Tulsi extract), will have the complementary properties of both the active and the peptide and as a net result will reduce or delay the symptoms of ageing by maintaining a healthy balance in the collagen synthesis and collagen breakdown in the dermal matrix of skin.

Example 3

Pentapeptide, Lysyl-Threonyl-Threonyl-Lysyl-Serine (SEQ ID No. 5) linked to the herbal active Boswellic acid (3-acetyl 11-keto Beta Boswellic acid) (From *Boswellia serrata* extract), will have the complementary properties of both the active and the peptide and as a net result will reduce or delay the symptoms of ageing by maintaining a healthy balance in the collagen synthesis and collagen breakdown in the dermal matrix of skin.

The Triterpenoid peptides thus are endowed with all the anti ageing modes of action (FIG. 1, Table 1) such as the Serine protease inhibitory activity, Antioxidant activity and collagen boosting activity for maintaining a healthy balance of collagen synthesis and collagen breakdown in the dermal matrix of the skin.

TABLE 1 showing the activity of triterpenoid peptides against elastase, collagenase and oxidants.

| Conc (mcg/ml) | % Elastase inhibitory activity | % Collagena se inhibitory activity | % DPPH scavenging activity |
|---|---|---|---|
| 500 | 85 | 40 | 35 |
| 300 | 75 | 37 | 30 |
| 250 | 66 | 36 | 22 |
| 125 | 30 | 20 | 20 |
| 100 | 25 | 16 | 12 |

The topical cosmetic compositions containing the natural extracts of the present invention may be prepared in liquid or solid form by mixing in with base ingredients, adjuvants and additives commonly used in the cosmetics field. Cosmetics in liquid or solid form include but are not limited to skin lotions, creams, lotions, and bath agents.

The compositions for topical application can also be used in Peel off and face mask cosmetic formulations.

INDUSTRIAL APPLICABILITY

As apparent from the above description, the natural compositions according to the present invention can be effectively for Anti ageing and Skin care applications. Although the preferred embodiments of the present invention have been disclosed for illustrative purposes, those skilled in the art will appreciate that various modifications, additions and substitutions are possible, without departing from the scope and spirit of the invention as disclosed in the accompanying claims.

CHEMICAL SYNTHESES OF PENTAPEPTIDE ANALOGUES

Acetyloleanoyl Lys (Z)-Thr (Bzl)-Thr (Bzl)-Lys (Z)-Ser (Bzl)-OBzl

Acetyloleanolic acid (5 GMs, 10 mmoles) is dissolved in 50 ml of chloroform and cooled to 0° C. 20 ml of freshly distilled thionyl chloride is added drop wise to the reaction mixture. The mixture was stirred at low temperature for 30 min and then at room temperature for 2 h. Solvents are then completely removed in vacuo and the residue is dried.

9.3 g of TFA.Lys (Z)-Thr (Bzl)-Thr (Bzl)-Lys (Z)-Ser (Bzl)-OBzl (9.3 GMs, 7.14 mmoles) is taken with 100 ml of chloroform and cooled to 0° C. Under stirring 5 ml of triethylamine is added and pH of this solution is adjusted to 8-9. The pentapeptide solution is cooled to 10° C. and under stirring acetyloleanoyl chloride solution prepared above (in 25 ml of chloroform) is slowly added. The mixture is stirred at low temperature for 15 min and at room temperature till completion of reaction. The reaction mixture is then washed with 10% $KHSO_4$ solution (3 times), water, saturated $NaHCO_3$ solution (3 times), water and saturated NaCl solution. It is finally dried over anhydrous $Na_2SO_4$ and concentrated in in vacuo. The residue is precipitated using ethyl acetate/petroleum ether (7:3), the precipitate is then filtered and dried in vacuo. Yield 13.4 g (80%). The mass spectrum indicated the desired m/e peak at 1673 and high resolution NMR was conforming to desired structure.

Acetyloleanoyl-Lys-Thr-Thr-Lys-Ser-OH
(acetyloleanoyl group linked to SEQ ID No. 2)

Acetyloleanoyl-Lys (Z)-Thr (Bzl)-Thr (Bzl)-Lys (Z)-Ser (Bzl)-OBzl (10 GMs, 6 mmoles) is mixed with 100 ml of 5% acetic acid in methanol and transferred to a hydrogenator. 2 g of 10% Pd—C is added to the reaction mixture Hydrogenation is carried out at a temperature of 60° C. using hydrogen pressure of 5 kg. After completion of reaction, catalyst was filtered off and the reaction mixture was concentrated in vacuo. The residue was precipitated by adding Acetonitrile. The solid was filtered and dried. Yield 5.6 g (90%). Mass spectrum showed molecular ion peak at 1045.

Preparation of Oleanoyl-Lys-Thr-Thr-Lys-Ser-OH
(oleanolic acid linked to SEQ ID No. 1)

Acetyloleanoyl-Lys-Thr-Thr-Lys-Ser-OH (acyloxy-oleanolyl group linked to SEQ ID No. 2) obtained above (5 GMs, 4.8 mmoles) was taken up in 25 ml of methanol and stirred. To this mixture 25 ml of 2M LiOH solution was added and stirred for 2 hours. Methanol was stripped from the reaction mixture. The aqueous solution washed with ethyl acetate and acidified with 1N HCl solution to pH 7-8. The aqueous solution was then evaporated to dryness. To the residue methanol was added and insoluble salts was filtered off. The solution was concentrated and precipitated using dry diethyl ether. The solid was then filtered and dried. Yield 4.1 g (85%). ES-MS spectrum showed molecular ion peak at m/e 1001(M-H).

Acetylursolyl-Lys (Z)-Thr (Bzl)-Thr (Bzl)-Lys (Z)-Ser (Bzl)-OBzl

Acetylursolic acid (5 GMs, 10 mmoles) is dissolved in 50 ml of chloroform and cooled to 0° C. 20 ml of freshly distilled thionyl chloride is added drop wise and mixture and stirred at low temperature for 30 min and then at room temperature for 2 h. Solvents are then completely removed in vacuo and the residue is dried.
TFA.Lys (Z)-Thr (Bzl)-Thr (Bzl)-Lys (Z)-Ser (Bzl)-OBzl (9.3 GMs, 7.14 mmoles) is taken 100 ml of chloroform and cooled to 0° C. Under stirring 5 ml of triethylamine is added and pH of this solution is adjusted to 8-9. The pentapeptide solution is cooled to 100° C. and under stirring acetylursolyl chloride above dissolved in 25 ml of chloroform is slowly added. The mixture is stirred at low temperature for 15 min and at room temperature till completion of reaction.
The reaction mixture is then washed with 10% $KHSO_4$ solution (3 times), water, saturated $NaHCO_3$ solution (3 times), water and saturated NaCl solution. It is finally dried over anhydrous $Na_2SO_4$ and concentrated in in vacuo. The residue is precipitated using 70% ethyl acetate in petroleum ether (60-80° C.). The precipitate is then filtered and dried in vacuo. Yield 13.4 g (80%).

Acetylursolyl-Lys-Thr-Thr-Lys-Ser-OH
(acetylursolyl group linked to SEQ ID No. 4)

Acetylursolyl-Lys (Z)-Thr (Bzl)-Thr (Bzl)-Lys (Z)-Ser (Bzl)-OBzl (10 GMs, 6 mmoles) is mixed with 100 ml of 5% acetic acid in methanol and transferred to a hydrogenator. 2 g of 10% Pd—C is added to the reaction mixture Hydrogenation is carried out at a temperature of 60° C. under hydrogen pressure of 5 kg. After completion of reaction, Pd—C is filtered off and the reaction mixture is concentrated at 45° C. in vacuo. The residue is precipitated by adding Acetonitrile. The precipitate is then filtered and dried. Yield 5.6 g (90%). Mass spectrum showed molecular ion peak m/e at 1045.

Preparation of Urosoyl-Lys-Thr-Thr-Lys'-Ser-OH
(Ursolic acid linked to SEQ ID No. 3)

Acetylursolyl-Lys-Thr-Thr-Lys-Ser-OH (acetylursolyl group linked to SEQ ID No. 4) (5 GMs, 4.8 mmoles) is taken in 25 ml of methanol and stirred. To this mixture 25 ml of 2M LiOH solution is added and mixture stirred for 2 hours. Methanol is now removed from the reaction mixture and aqueous solution is washed with ethyl acetate and acidified with 1N HCl solution. pH adjusted to 7-8. The aqueous solution is then evaporated to dryness. To the residue methanol is added. Insoluble salts are filtered off. The solution is concentrated and precipitated using dry diethyl ether. The precipitate is then filtered and dried. Yield 4.1 g (85%). ES-MS spectrum showed molecular ion peak at m/e 1001(M-H).

Preparation of 3-Acetyl-11-Keto-β-Boswellic acid-Lys (Z)-Thr (Bzl)-Thr (Bzl)-Lys (Z)-Ser (Bzl)-OBzl Acetyl-11-Keto-β-Boswellic acid (5.1 GMs, 10 mmoles) is dissolved in 50 ml of chloroform and cooled to 0° C. 20 ml of freshly distilled thionyl chloride is added drop wise to the reaction mixture and stirred at low temperature for 30 min. The reaction mixture is then stirred at room temperature for 2 h. Solvents are then completely removed in vacuo and the residue is dried. It is then dissolved in 25 ml of chloroform. In the mean time TFA.Lys (Z)-Thr (Bzl)-Thr (Bzl)-Lys (Z)-Ser (Bzl)-OBzl (9.3 GMs, 7.14 mmoles) is taken with 100 ml of chloroform and cooled to 0° C. Under stirring 5 ml of triethylamine is added and pH of this solution is adjusted to 8-9. The pentapeptide solution is cooled to 10° C. and under stirring acetyl-keto-β-boswellyl chloride solution is slowly added. The mixture is stirred at low temperature for 15 min and at then room temperature till completion of reaction. Now the reaction mixture is washed with 10% $KHSO_4$ solution (3 times), water, saturated $NaHCO_3$ solution (3 times), water and saturated NaCl solution. It is finally dried over anhydrous $Na_2SO_4$ and concentrated in in vacuo. The residue is precipitated using 70% ethyl acetate in petroleum ether (60-80° C.). The precipitate is then filtered and dried in vacuo. Yield 12.5 g (74%) (3-acetyl-11-keto-beta-boswellyl-Lys-Thr-Thr-Lys-Ser i.e. 3-acetyl-11-keto-beta-boswellyl group linked to SEQ ID No. 6).

Preparation of Acetyl-keto-β-boswellyl-Lys-Thr-Thr-Lys-Ser-OH (Acetyl-Keto-β-boswellyl group linked to SEQ ID No. 8)

Acetyl-keto-β-boswellyl-Lys (Z)-Thr (Bzl)-Thr (Bzl)-Lys (Z)-Ser (Bzl)-OBzl (10 GMs, 5.9 mmoles) is mixed with 100 ml of 5% acetic acid in methanol and transferred to a hydrogenator. 2 g of 10% Pd—C is added to the reaction mixture Hydrogenation is carried out at a temperature of 60° C. and hydrogen pressure of 5 kg. After completion of reaction, Pd—C is filtered off and the reaction mixture is concentrated at 45° C. in vacuo. The residue is precipitated by adding Acetonitrile. The precipitate is then filtered and dried. Yield 5.6 g (90%).

Preparation of Keto-β-boswellyl-Lys-Thr-Thr-Lys-Ser-OH (Keto-β-boswellyl linked to SEQ ID No. 7)

Acetyl-keto-β-boswellyl-Lys-Thr-Thr-Lys-Ser-OH (Acetyl-keto-β-boswellyl group linked to SEQ ID No. 8) (5 GMs, 4.7 mmoles) is taken in 25 ml of methanol and stirred. To this mixture 25 ml of 2M LiOH solution is added and stirred for 2 h. Methanol is removed from the reaction mixture. The aqueous solution is washed with ethyl acetate and acidified with 1N HCl solution. pH adjusted to 7-8. The aqueous solution is then evaporated to dryness. To the residue methanol is added. Insoluble salts are filtered off. The solution is concentrated and precipitated using dry diethyl ether. The precipitate is then filtered and dried. Yield 4 g (85%).

The sequence listing of peptides is in the attached Appendix I and has also been submitted in electronic form via EFS web as file named sequencerev1.txt

What is claimed is:

1. A peptide containing the sequence Lysyl-Threonyl-Threonyl-Lysyl-Serine (SEQ ID No. 1) with Oleanolic acid attached to the terminal lysine as shown hereunder

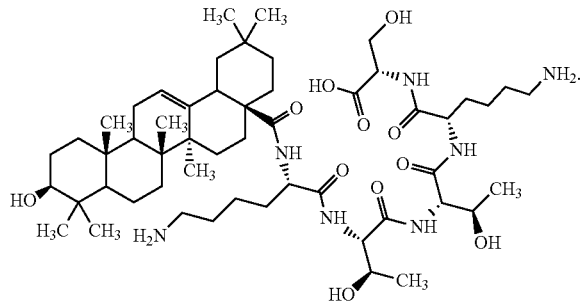

2. A cosmetic composition comprising the compound of claim 1 and one or more cosmetic or manufacturing adjuncts selected from a group consisting of a sunscreen, a skin-lightening agent, a skin-tanning agent, an antioxidant, a perfume, an opacifier, a preservative, a colorant, an emulsifier, a thickener and a buffer formulated in a dermatologically acceptable vehicle.

3. The composition of claim 2, wherein the dermatologically-acceptable vehicle is selected from the group consisting of water, a buffered aqueous solution, a liquid emollient, a solid emollient, a silicone oil and a solvent.

4. The composition of claim 2, wherein the composition is in the form of a lotion, cream or mousse for topical application.

* * * * *